(12) United States Patent
Tuan

(10) Patent No.: US 6,415,177 B1
(45) Date of Patent: Jul. 2, 2002

(54) TRANSCUTANEOUS ELECTRICAL NERVE STIMULATOR

(76) Inventor: Wei Tuan, 12F, No. 156, Sec. 1, Chien Kuo North Road, Taipei (TW), 104

( * ) Notice: Subject to any disclaimer, the term of this patent is extended or adjusted under 35 U.S.C. 154(b) by 0 days.

(21) Appl. No.: 09/564,948

(22) Filed: May 5, 2000

(51) Int. Cl.[7] .................................. A61N 1/00
(52) U.S. Cl. ............................................. 607/3
(58) Field of Search ................. 607/3, 96–99, 607/114

(56) References Cited

U.S. PATENT DOCUMENTS 4,763,657 A * 8/1988 Chen et al.
5,107,832 A * 4/1992 Guilbert et al.

* cited by examiner

Primary Examiner—Scott M. Getzow
(74) Attorney, Agent, or Firm—Charles E. Baxley

(57) ABSTRACT

A transcutaneous electrical nerve stimulator includes a casing for engaging onto a patient, and a heater disposed in the casing for warming the patient. A medicine member is engaged in the casing and heated by the heater to distribute the medicine into the patients. A spring-biased projection may be used to disengage the medicine member from the casing. A control device has one or more batteries electrically coupled to the heater for actuating and energizing the heater. A conductive member may receive and supply the gentle electricity to the conductive member.

13 Claims, 6 Drawing Sheets

TRANSCUTANEOUS ELECTRICAL NERVE STIMULATOR

BACKGROUND OF THE INVENTION

1. Field of the Invention

The present invention relates to a nerve stimulator, and more particularly to a transcutaneous electrical nerve stimulator.

2. Description of the Prior Art

Typical transcutaneous electrical nerve stimulators comprise two terminals directly engaged with the users, particularly the patients, and may generate electric shocks to stimulate the nerves or the vital points recognized in acupuncture. In a so-called gate control theory, the transcutaneous electrical nerve stimulator is used and last for a long time, in order to stimulate or to close the gates that control the pains of the vertebrae. However, actually, the nerves and the vital points recognized in acupuncture or the gates are paralyzed by the electric shocks such that the patients do not feel the pain. The transcutaneous electrical nerve stimulator may also be used to generate a low frequency and high intensity shock in order to stimulate or to block the nerves and to prevent the pains from being transmitted to the brain. The typical transcutaneous electrical nerve stimulators may hurt or damage the nerves or the vital points with the electric shocks.

The present invention has arisen to mitigate and/or obviate the afore-described disadvantages of the conventional transcutaneous electrical nerve stimulators.

SUMMARY OF THE INVENTION

The primary objective of the present invention is to provide a transcutaneous electrical nerve stimulator for stimulating the nerves and the vital points recognized in acupuncture with gentle electric shocks.

The other objective of the present invention is to provide a transcutaneous electrical nerve stimulator for permeating or distributing the Chinese herbal medicine into the patients.

The further objective of the present invention is to provide a transcutaneous electrical nerve stimulator for generating a vibration in order to massage the patients.

In accordance with one aspect of the invention, there is provided a transcutaneous electrical nerve stimulator comprising a casing for engaging onto a patient, and a heater disposed in the casing for warming the patient, particularly for warming or for stimulating the nerves and the vital points recognized in acupuncture.

A medicine member is further provided and engaged in the casing and aligned with the heater for being heated by the heater. The medicine member includes a ceramic body having a Chinese herbal medicine engaged therein or is directly made of the Chinese herbal medicine. A device is further provided for disengaging the medicine member from the casing and includes a projection slidably received in the casing and engaged with the medicine member for disengaging the medicine member from the casing.

The casing includes a resilient member having the projection extended therefrom for engaging with the medicine member and for disengaging the medicine member from the casing. The heater includes an orifice formed therein for receiving the projection.

A control device is further provided and electrically coupled to the heater of the casing. The control device includes a prong provided therein, the casing includes a socket provided therein for receiving the prong.

A device is further provided for vibrating the casing and includes a control device, and a vibrator received in the control device for generating a vibration and for vibrating or for massaging the patients via the casing. A conductive member is further attached to the casing, and means for supplying an electricity to the conductive member. The conductive member may be a conductive silicone member for receiving the electricity or the electric current and for transmitting the electric current to the patients. The control device has one or more batteries disposed therein for energizing the electric parts or elements.

Further objectives and advantages of the present invention will become apparent from a careful reading of a detailed description provided hereinbelow, with appropriate reference to accompanying drawings.

DETAILED DESCRIPTION OF THE PREFERRED EMBODIMENT

Figure 1:
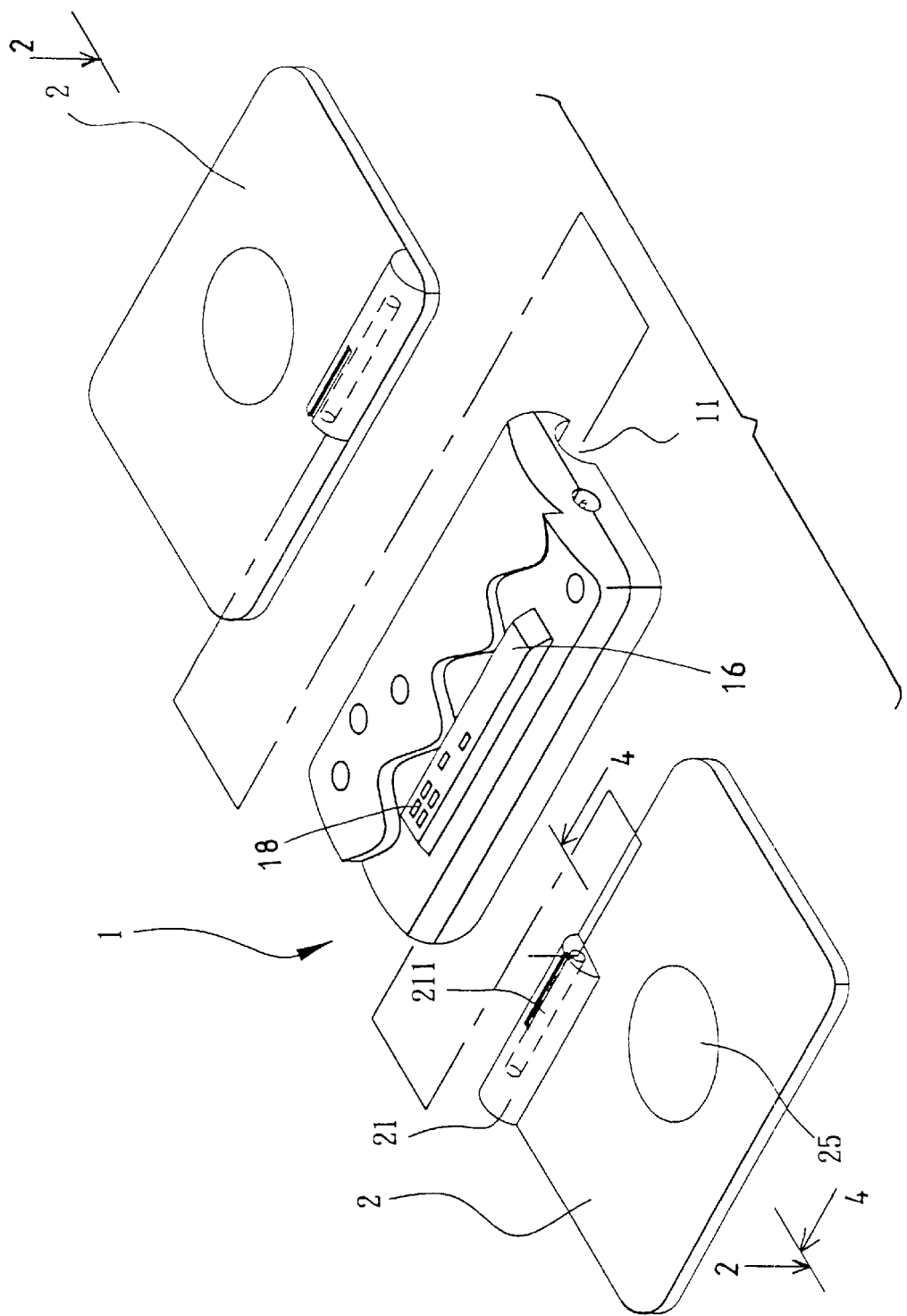
FIG. 1 is an exploded view of a transcutaneous electrical nerve stimulator in accordance with the present invention.
Figure 2:
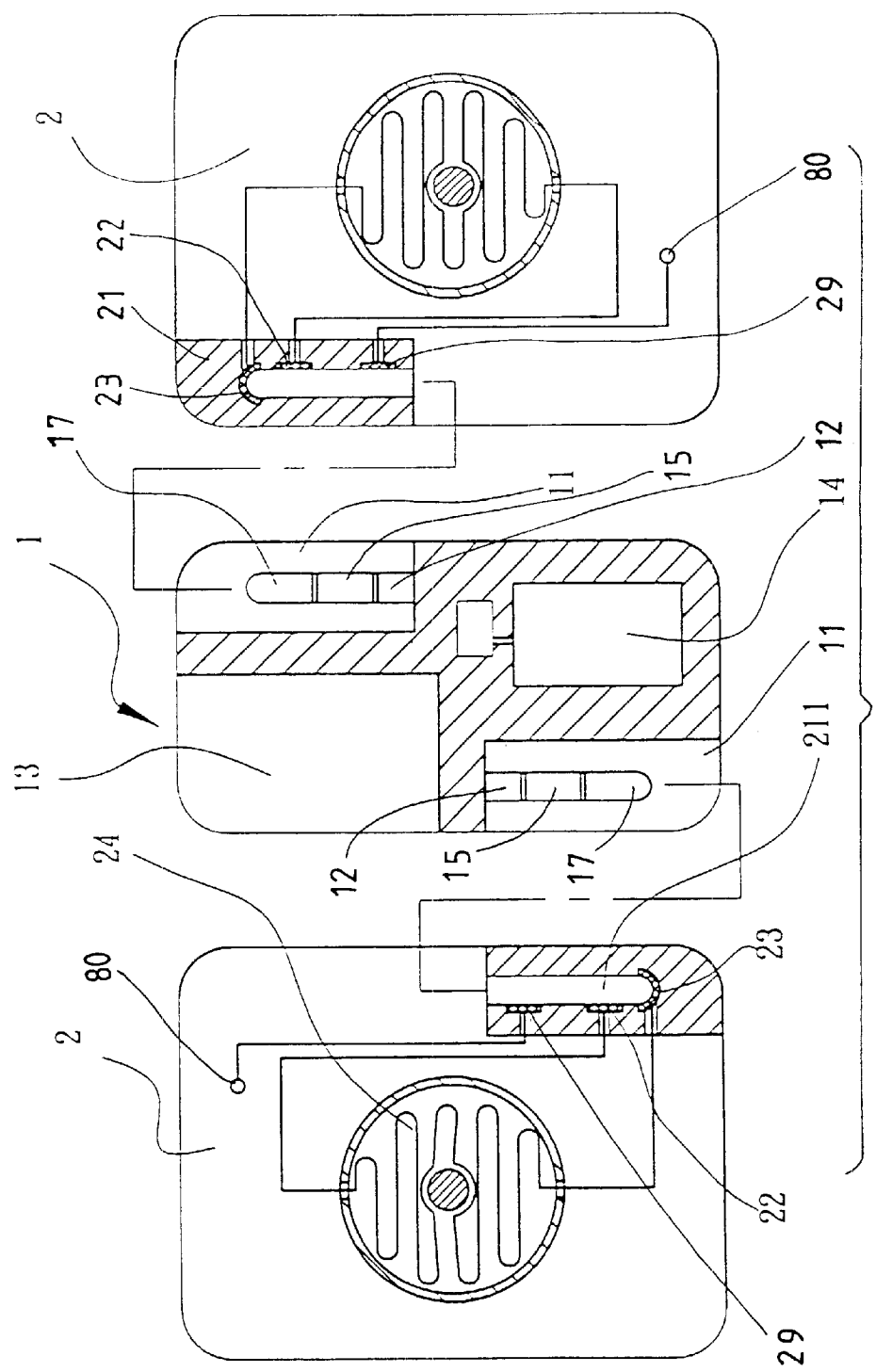
FIG. 2 is an exploded and cross sectional view taken along lines 2—2 of FIG. 1.
Figure 3:
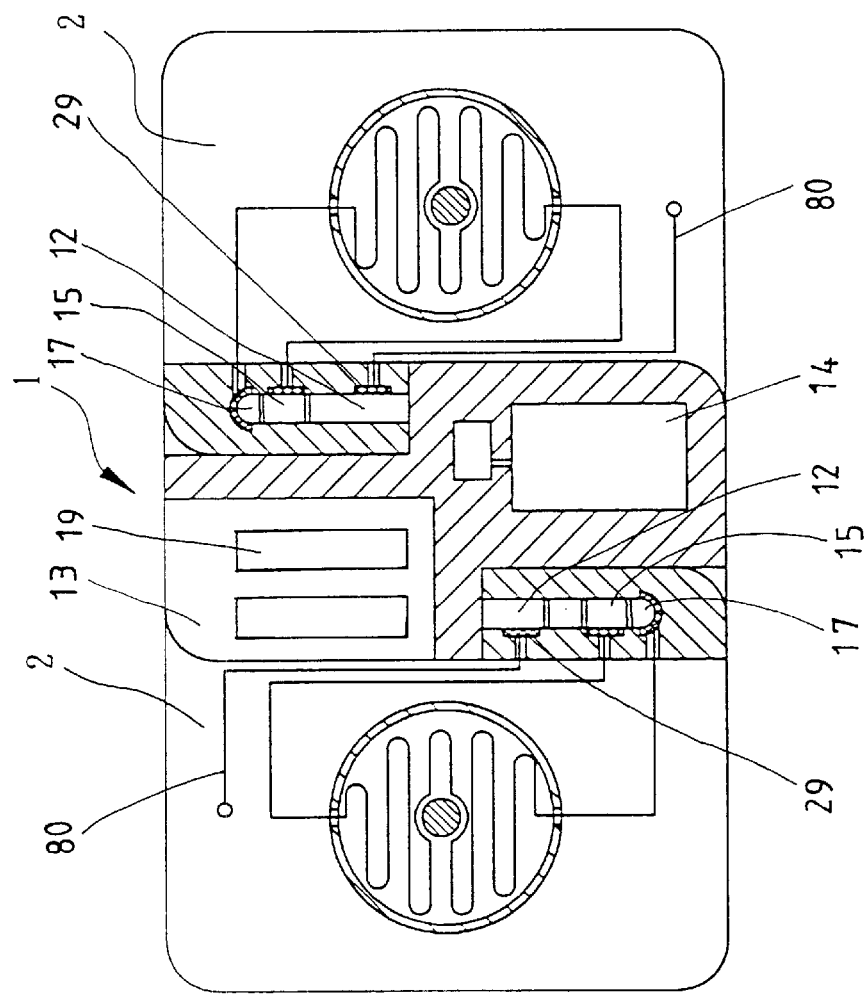
FIG. 3 is a cross sectional view of the elements as shown in FIG. 2 which are secured or coupled together.

Referring to the drawings, and initially to FIGS. 1–4, a transcutaneous electrical nerve stimulator in accordance with the present invention comprises a control device 1 including an electric circuit or device provided therein having such as the transformers, the transistors, the processor units 16. the resistors, etc., coupled thereto. The control device 1 includes a number of switches 18 for controlling the elements of the control device 1 and includes a chamber 13 formed therein for receiving one or more batteries 19 which may energize the electric elements. The control device 1 further includes a vibrating motor or a vibrator 14 disposed therein for generating vibrations to massage the patients. The control device 1 includes one or more spaces 11 formed therein and includes one or more prongs 12 extended inward of the respective spaces 11 of the control device 1. The prongs 12 each includes two or more conductors or electrodes 15, 17 provided thereon. For example, as shown in FIGS. 2 and 3, the prongs 12 each includes one positive electrode 17 and two negative electrodes 15 provided thereon.

The transcutaneous electrical nerve stimulator further includes one or more boards or casings 2 each having a protrusion 21 for rotatably engaging into the respective spaces 11 of the control device 1 and each having a hole or a socket 211 formed in the respective protrusions 21 for receiving the respective prongs 12 of the control device 1. The casings 2 each includes a heater device 24, particularly an electric heater, disposed therein and coupled to two terminals or conductors 22, 23 which are coupled to the positive and the negative electrodes 17, 15 of the prongs 12 for being energized by the batteries 19 of the control device 1. The casings 2 each includes a conductive silicon member 20 secured therein, particularly disposed on the peripheral portion thereof or disposed around the heater device 24 (FIGS. 4, 5), and each includes one or more conductors 29 disposed in the respective protrusions 21 and engaged with the other negative electrode 15 of the prongs 12 for allowing the electric current or shocks or the other electricities to be transmitted to the conductive silicon member 20 and for stimulating the nerves and the vital points recognized in acupuncture with gentle electric shocks or with the electric current.

It is to be noted that the metal electrodes or the metal terminals are not directly engaged with the patients such that the patients will not feel cold by contacting with the metal terminals. In addition, the electric current or shocks are transmitted to the patients via the conductive silicon member 20 and may be attenuated or smoothed by the conductive silicon member 20 such that the nerves and the vital points recognized in acupuncture will not be damaged or hurt by the gentle electric shocks or current from the conductive silicon member 20. The vibrations generated by the vibrator 14 may also be transmitted to the patients via the casings 2.

Figure 4:
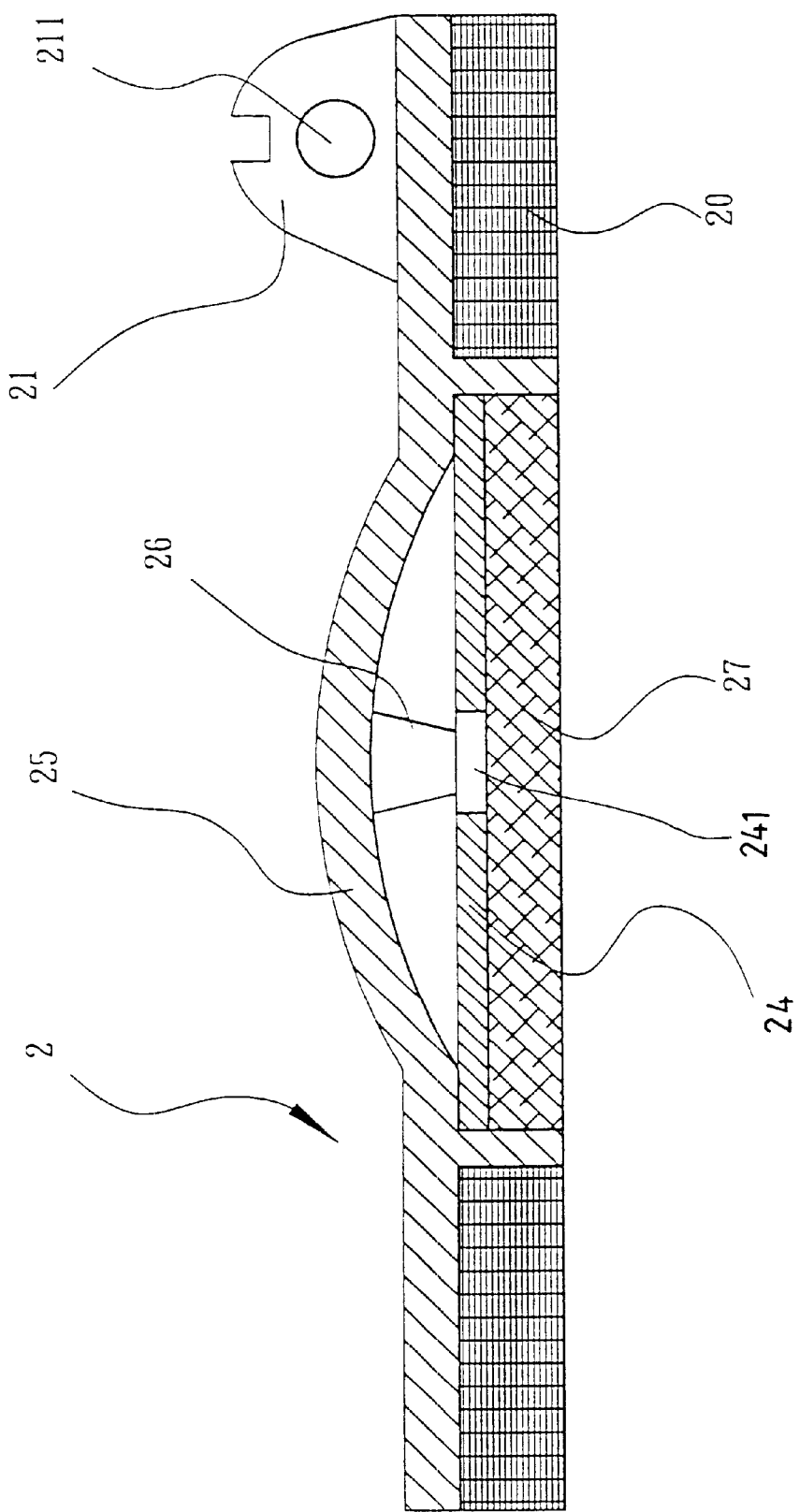
FIG. 4 is a cross sectional view taken along lines 4—4 of FIG. 1.
Figure 5:
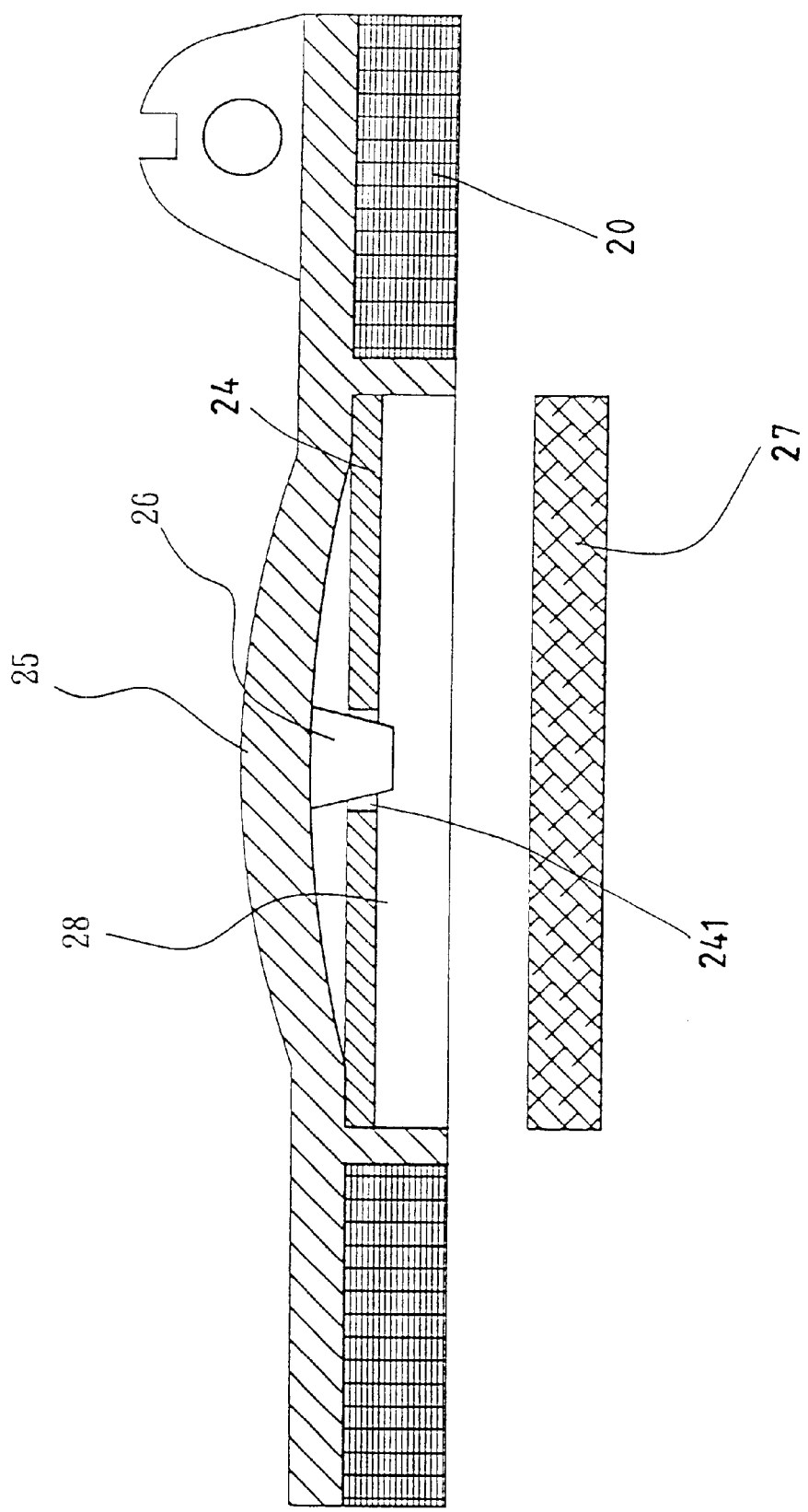
FIG. 5 is a cross sectional view similar to FIG. 4. illustrating the operation of the transcutaneous electrical nerve stimulator.

Referring next to FIG. 5 and again to FIG. 4, the casings 2 each includes a recess 28 formed therein for receiving the heater device 24 and/or a medicine member 27 therein. The medicine member 27 may be a block made of Chinese herbal medicine or may be a ceramic panel having the Chinese herbal medicine and/or the perfume material or the perfume oil engaged therein. The heater device 24 may be used to directly heat or to warm the vital points recognized in acupuncture or may be used to heat the medicine member 27 in order to permeate or distribute the Chinese herbal medicine into the vital points recognized in acupuncture of the patients. The casing 2 includes a resilient member 25, such as a resilient bulge provided therein and aligned with the heater device 24 or the medicine member 27, and includes a projection 26 extended from the resilient member 25 and extendible through an orifice 241 of the heater device 24 for disengaging the medicine member 27 from the casing 1 by depressing the resilient member 25. The medicine member 27 may thus be replaced with the other one.

Figure 6:
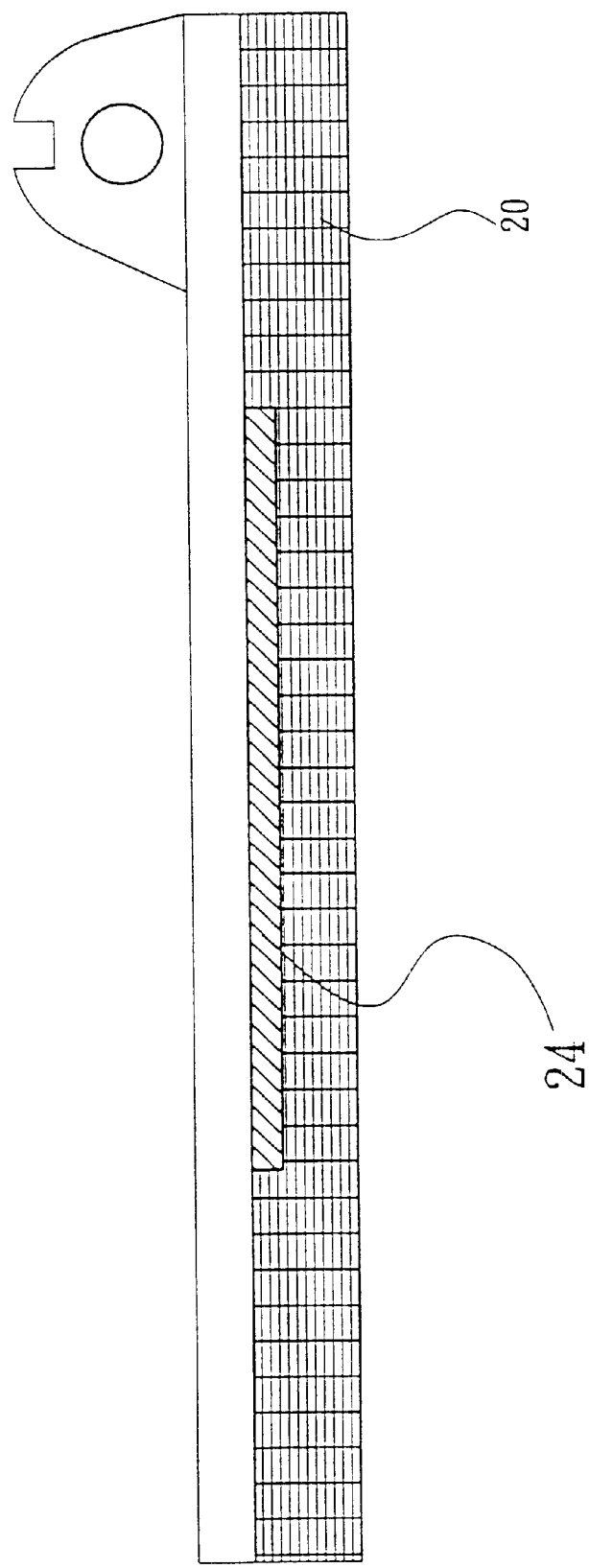
FIG. 6 is a cross sectional view similar to FIGS. 4 and 5, illustrating the other application of the transcutaneous electrical nerve stimulator.

Referring next to FIG. 6, the silicon member 20 and the medicine member 27 may be combined or mixed together as a unit having the Chinese herbal medicine engaged therein which may also be distributed into the patients by the heater device 24. After the Chinese herbal medicine has been consumed or has been used up, the casing 2 may be discarded and may be replaced with the other one.

Accordingly, the transcutaneous electrical nerve stimulator in accordance with the present invention may be used for stimulating the nerves and the vital points recognized in acupuncture with gentle electric shocks, or for permeating or distributing the Chinese herbal medicine into the patients, or for generating a vibration in order to massage the patients.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:
1. A transcutaneous electrical nerve stimulator comprising:
   a casing for engaging onto a patient,
   a heater disposed in said casing for warming the patient, and
   a medicine member engaged in said casing and aligned with said heater for being heated by said heater.
2. The transcutaneous electrical nerve stimulator according to claim 1 wherein said medicine member includes a ceramic body having a Chinese herbal medicine engaged therein.
3. The transcutaneous electrical nerve stimulator according to claim 1, further comprising means for disengaging said medicine member from said casing.
4. The transcutaneous electrical nerve stimulator according to claim 3, wherein said disengaging means includes a projection slidably received in said casing and engaged with said medicine member for disengaging said medicine member from said casing.
5. The transcutaneous electrical nerve stimulator according to claim 4, wherein said casing includes a resilient member having said projection extended therefrom.
6. The transcutaneous electrical nerve stimulator according to claim 4, wherein said heater includes an orifice formed therein for receiving said projection.
7. The transcutaneous electrical nerve stimulator according to claim 1 further comprising a control device electrically coupled to said heater of said casing.
8. The transcutaneous electrical nerve stimulator according to claim 1 further comprising a conductive member attached to said casing, and means for supplying an electricity to said conductive member.
9. The transcutaneous electrical nerve stimulator according to claim 8, wherein said conductive member is a conductive silicone member.
10. The transcutaneous electrical nerve stimulator according to claim 1 further comprising a control device having at least one battery provided therein.
11. A transcutaneous electrical nerve stimulator comprising:
    a casing for engaging onto a patient,
    a heater disposed in said casing for warming the patient, and
    a control device electrically coupled to said heater of said casing, said control device including a prong provided therein, said casing including a socket provided therein for receiving said prong.
12. A transcutaneous electrical nerve stimulator comprising:
    a casing for engaging onto a patient,
    a heater disposed in said casing for warming the patient, and
    means for vibrating said casing.
13. The transcutaneous electrical nerve stimulator according to claim 12, wherein said vibrating means includes a control device, and a vibrator received in said control device.

* * * * *